US010874701B2

(12) United States Patent
Kim et al.

(10) Patent No.: US 10,874,701 B2
(45) Date of Patent: *Dec. 29, 2020

(54) LACTIC ACID BACTERIA CAPABLE OF PREVENTING AND/OR TREATING SENESCENCE AND DEMENTIA

(71) Applicant: UNIVERSITY-INDUSTRY COOPERATION GROUP OF KYUNG HEE UNIVERSITY, Gyeonggi-Do (KR)

(72) Inventors: Dong-Hyun Kim, Seoul (KR); Myung Joo Han, Seoul (KR); Il-Hoon Jung, Gyeonggi-Do (KR); Myung-Ah Jung, Gyeonggi-Do (KR)

(73) Assignee: UNIVERSITY-INDUSTRY COOPERATION GROUP OF KYUNG HEE UNIVERSITY, Yongin-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/297,955

(22) Filed: Oct. 19, 2016

(65) Prior Publication Data
US 2017/0049828 A1 Feb. 23, 2017

Related U.S. Application Data

(62) Division of application No. 14/421,714, filed as application No. PCT/KR2013/007410 on Aug. 16, 2013, now abandoned.

(30) Foreign Application Priority Data

Aug. 16, 2012 (KR) .......................... 10-2012-0089714

(51) Int. Cl.
| | | |
|---|---|---|
| *A61K 35/747* | (2015.01) | |
| *C12N 1/20* | (2006.01) | |
| *C12R 1/25* | (2006.01) | |
| *C12R 1/225* | (2006.01) | |
| *A23L 33/135* | (2016.01) | |
| *A61K 35/00* | (2006.01) | |

(52) U.S. Cl.
CPC .......... *A61K 35/747* (2013.01); *A23L 33/135* (2016.08); *C12N 1/20* (2013.01); *C12R 1/225* (2013.01); *C12R 1/25* (2013.01); *A23V 2002/00* (2013.01); *A61K 2035/11* (2013.01)

(58) Field of Classification Search
None
See application file for complete search history.

(56) References Cited

U.S. PATENT DOCUMENTS

| | | |
|---|---|---|
| 7,557,089 B2 | 7/2009 | Zhang et al. |
| 7,619,005 B2 | 11/2009 | Epstein et al. |
| 8,404,711 B2 | 3/2013 | Beattie et al. |
| 8,440,426 B2 | 5/2013 | Fujita et al. |
| 8,940,789 B2 | 1/2015 | Kusano et al. |
| 2010/0003274 A1* | 1/2010 | Nonaka ..................... A23L 2/52 424/195.17 |
| 2011/0027348 A1 | 2/2011 | Feher |
| 2011/0142990 A1 | 6/2011 | Jacob |
| 2015/0306158 A1 | 10/2015 | Kim et al. |

OTHER PUBLICATIONS

Kim et al., ((2011), Appl. Biochem. Biotechnol. 165, 1107-1110).*
He et al., ((2011), Journal of Bioscience and Bioengineering 112, 188-193).*
Park et al., ((2010), Journal of Korean Soc. Food Sci. Nutr. vol. 39, pp. 1691-1694).*
Hu et al., ((2004), J. Agric. Food Chem. vol. 52, pp. 1691-1694).*
Weon et al., ((2013), Evidence Based Complementary and Alternative Medicine, vol. 2013, Article ID 464576, 7 pages).*
Kanekar et al., Food Microbiol., 9:245-249 (1992) (Year: 1992).*
Hayes et al, J. Food Sci., 42(6):1527-1532 (1977) (Year: 1977).*
Jung et al., "*Lactobacillus pentosus* var. plantarum C29 protects scopolamine-induced memory deficit in mice", Journal of Applied Microbiology, vol. 113, Issue 6, pp. 1498-1506.
Mendiola-Precoma et al., "Therapies for Prevention and Treatment of Alzheimer's Disease", BioMed Research International, vol. 2016, Article ID 2589276, 17 pages.
Nedelcheva et al., "Probiotic Strain Lactobacillus Plantarum NBIMCC 2415 with Antioxidant Activity as a Starter Culture in the Production of Dried Fermented Meat Products", Biotechnol & Biotechnol Eq, 2010.
Wang et al., "Lactobacillus plantarum ZLP001: In Vitro Assessment of Antioxidant Capacity and Effect on Growth Performance and Antioxidant Status in Weaning Piglets".
Virtanen et al., .(Journal of Applied Microbiology, vol. 102 (2007), pp. 106-115.
Grajek et al., Acta Biochimica Polonica, vol. 52 No. 3/2005, 665-671.

(Continued)

*Primary Examiner* — Thomas J. Visone
(74) *Attorney, Agent, or Firm* — Sughrue Mion, PLLC

(57) ABSTRACT

The present invention provides a novel lactic acid bacterium having antioxidant and anti-aging functions and a dementia alleviation effect, and more specifically, provides *Lactobacillus pentosus* var. *plantarum* C29 KCCM11291P and *Lactobacillus curvatus* C3 KCCM430009. In addition, the present invention provides an antioxidant and anti-aging pharmaceutical composition and a dietary supplement containing the *Lactobacillus pentosus* var. *plantarum* C29 KCCM11291P or *Lactobacillus curvatus* C3 KCCM430009 of the present invention as an active ingredient, and a composition for preventing or treating dementia and a dietary supplement for preventing or alleviating dementia, containing *Lactobacillus pentosus* var. *plantarum* C29 KCCM11291P or *Lactobacillus curvatus* C3 KCCM430009 as an active ingredient. Additionally, the present invention provides a composition for preventing or treating dementia, containing a fermentation composition, as an active ingredient, fermented by *Lactobacillus pentosus* var. *plantarum* C29 KCCM11291P or *Lactobacillus curvatus* C3 KCCM430009.

14 Claims, 7 Drawing Sheets

Specification includes a Sequence Listing.

(56) References Cited

OTHER PUBLICATIONS

Office Action cited in U.S. Appl. No. 14/421,714 dated Nov. 16, 2016.
Office Action cited in U.S. Appl. No. 14/421,714 dated Apr. 21, 2017.
Office Action cited in U.S. Appl. No. 15/641,873 dated Jan. 10, 2018.

* cited by examiner

[C-29 16S rDNA sequence (1428bp)]

Homology with *Lactobacillus pentosus* strain LS3 16S ribosomal RNA gene 1427/1428 (99.9%)
Homology with *Lactobacillus plantarum* strain BIM B-536 16S ribosomal RNA gene 1427/1428 (99.9%)

ACGAACTCTGGTATTGATTGGTGCTTGCATCATGATTTACATTTGAGTGAGTGGCGAACTGGTGAGTAACA
CGTGGGAAACCTGCCCAGAAGCGGGGGATAACACCTGGAAACAGATGCTAATACCGCATAACAACTTGG
ACCGCATGGTCCGAGTTTGAAAGATGGCTTCGGCTATCACTTTTGGATGGTCCCGCGGCGTATTAGCTAGA
TGGTGGGGTAACGGCTCACCATGGCAATGATACGTAGCCGACCTGAGAGGGTAATCGGCCACATTGGGAC
TGAGACACGGCCCAAACTCCTACGGGAGGCAGCAGTAGGGAATCTTCCACAATGGACGAAAGTCTGATG
GAGCAACGCCGCGTGAGTGAAGAAGGGTTTCGGCTCGTAAAACTCTGTTGTTAAAGAAGAACATATCTGA
GAGTAACTGTTCAGGTATTGACGGTATTTAACCAGAAAGCCACGGCTAACTACGTGCCAGCAGCCGCGGT
AATACGTAGGTGGCAAGCGTTGTCCCGGATTTATTGGGCGTAAAGCGAGCGCAGGCGGTTTTTTAAGTCTG
ATGTGAAAGCCTTCGGCTCAACCGAAGAAGTGCATCGGAAACTGGGAAACTTGAGTGCAGAAGAGGACA
GTGGAACTCCATGTGTAGCGGTGAAATGCGTAGATATATGGAAGAACACCAGTGGCGAAGGCGGCTGTCT
GGTCTGTAACTGACGCTGAGGCTCGAAAGTATGGGTAGCAAACAGGATTAGATACCCTGGTAGTCCATAC
CGTAAACGATGAATGCTAAGTGTTGGAGGGTTTCCGCCCTTCAGTGCTGCAGCTAACGCATTAAGCATTCC
GCCTGGGGAGTACGGCCGCAAGGCTGAAACTCAAAGGAATTGACGGGGGCCCGCACAAGCGGTGGAGC
ATGTGGTTTAATTCGAAGCTACGCGAAGAACCTTACCAGGTCTTGACATACTATGCAAATCTAAGAGATTA
GACGTTCCCTTCGGGGACATGGATACAGGTGGTGCATGGTTGTCGTCAGCTCGTGTCGTGAGATGTTGGGT
TAAGTCCCGCAACGAGCGCAACCCTTATTATCAGTTGCCAGCATTAAGTTGGGCACTCTGGTGAGACTGCC
GGTGACAAACCGGAGGAAGGTGGGGATGACGTCAAATCATCATGCCCCTTATGACCTGGGCTACACACGT
GCTACAATGGATGGTACAACGAGTTGCGAACTCGCGAGAGTAAGCTAATCTCTTAAAGCCATTCTCAGTTC
GGATTGTAGGCTGCAACTCGCCTACATGAAGTCGGAATCGCTAGTAATCGCGGATCAGCATGCCGCGGTG
AATACGTTCCCGGGCCTTGTACACACCGCCCGTCACACCATGAGAGTTTGTAACACCCAAAGTCGGTGGG
GTAACCTTTTAGGAACCAGCCGCCT

FIG. 1

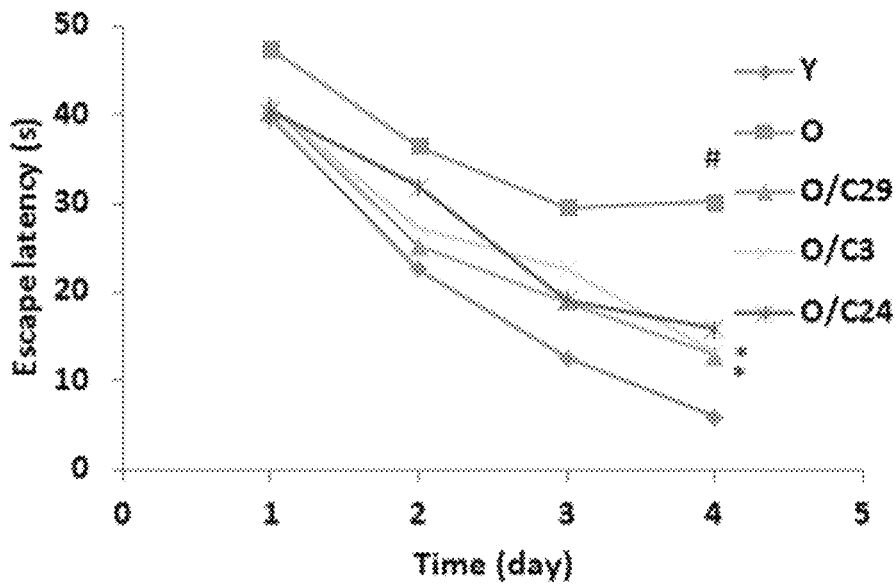

FIG. 10

[C3 sequence (893bp)]

Homology with *Lactobacillus curvatus* gene for 16S rRNA 864/866 (99%)

AGTCGTAACAAGGTAACCGTAGAAGTCTTGATTCGATAACATTTGAGTGAGTGGCGGACGGGTGAGTAACACG
TGGGTAACCTGCCCTAAAGTGGGGGATAACATTTGGAAACAGATGCT_ATACCGCATAAAACCTAGCACCGCA
TGGTGCAAGGTTGAAAGATGGTTTCGGCTATCACTTTAGGATGGACCCGCGGTGCATTAGTTAGTTGGTGAGG
TAAAGGCTCACCAAGACCGTGATGCATAGCCGACCTGAGAGGGTAATCGGCCACACTGGGACTGAGACACG
GCCCAGACTCCTACGGGAGGCAGCAGTAGGGAATCTTCCACAATGGACGAAAGTCTGATGGAGCAACGCCG
CGTGAGTGAAGAAGGTTTTCGGATCGTAAAACTCTGTTGTTGGAGAAGAACGTATTTGATAGTAACTGATCAG
GTAGTGACGGTATCCAACCAGAAAGCCACGGCTAACTACGTGCCAGCAGCCGCGGTAATACGTAGGTGGCAA
GCGTTGTCCGGATTTATTGGGCGTAAAGCGAGCGCAGGCGGTTTCTTAAGTCTGATGTGAAAGCCTTCGGCTC
AACCGAAGAAGTGCATCGGAAACTGGGAAACTTGAGTGCAGAAGAGGACAGTGGAACTCCATGTGTAGCGG
TGAAATGCGTAGATATATGGAAGAACACCAGTGGCGAAGGCGGCTGTCTGGTCTGTAACTGACGCTGAGGCTC
GAAAGCATGGGTAGCAAACAGGATTAGATACCCTGGTAGTCCATGCCGTAAACGATGAGTGCTAGGTGTTGGA
GGGTTTCCGCCCTTCAGTGCCGCAGCTAACGCATTAAGCACTCCGCCTGGGGAGTACGACCGCAAGGTTGAA
ACTCAAAGGAATTGACGGGGGCCCGC

FIG. 11

LACTIC ACID BACTERIA CAPABLE OF PREVENTING AND/OR TREATING SENESCENCE AND DEMENTIA

CROSS REFERENCE TO RELATED APPLICATION

This Application is a division of U.S. patent application Ser. No. 14/421,714, filed Feb. 13, 2015, which is a 371 Application of International Application No. PCT/KR2013/007410, filed Aug. 16, 2013, which claims the benefit of Korea Patent Application No. KR10-2012-0089714, filed Aug. 16, 2012, the disclosures of which are incorporated herein in their entirety.

BACKGROUND

Technical Field

The present invention relates to a novel lactic acid bacterium isolated from Kimchi, and more specifically, relates to novel *Lactobacillus pentosus* var. *plantarum* C29 and *Lactobacillus curvatus* C3 having an activity for preventing and/or treating aging (senescence) and dementia.

Background Art

To delay an aging process is one of important health challenges in a modern society rapidly proceeding into an aging society. In Korea, the population aged 65 or more comprised 11.3% in 2010, and is anticipated to rapidly increase to 37.3%. In such the aging society, it is anticipated that a disease morbidity rate is increased and enormous medical expenses are expected, as well as it is anticipated that a rapid growth of senile disease such as dementia becomes to be problematic socially.

A process progressing the aging is affected by a genetic, environment, and complex action of a lifestyle, and is followed by various morphological, biochemical changes, in particular, an increase of oxidation stress and inflammation reaction are believed as a major reason involving in a promotion of aging. The oxidation stress is caused by an increase of a generation of reactive oxygen species having a strong reactivity or a reduction of an anti-oxidative defense mechanism in a body, and as a result, biomacromolecules such as DNA, etc. are destroyed, cellular damages are caused to promote the aging, and a risk of age-associated diseases, such as degenerative neuronal disease including dementia, cancer, cardiovascular diseases, etc. is increased.

Alder et al. (Adler A S, Sinha S, Kawahara T L, Zhang J Y, Segal E, Chang H Y. Motif module map reveals enforcement of aging by continuous NF-kappa B activity. Genes Dev. 2007; 21:3244-57) proved a relevance between NF-κB activation motif and a unit regulating the aging process and thus demonstrated that the inflammation reaction mediated by NF-κB and the aging process are very closely associated with each other. In addition, it is known that the aging activates PI3K/AKT, which phosphorylates FOXO3, and ROS generation cannot be inhibited and thus a gene variation, etc. are occurred.

Dementia which is one of aging diseases is occurred by chronic or progressive diseases of brain, and regression, degeneration of brain tissues, and aging-central nervous system infection (neurosyphilis, tuberculous meningitis, viral encephalitis, etc.), cerebral infarction, brain damage, toxic metabolic disorder, nervous system disease (Parkinson's disease) and the like, have been known to be a major reason for causing the dementia. Dementia includes Alzheimer's disease, vascular dementia, and other mixed forms, 50~60% of old dementia patients aged 65 or more have Alzheimer's dementia and remaining 10~15% of them have the mixed forms of such two (2) diseases. It is known that a waste in brain, β-amyloid (Aβ) is a major cause of the disease of Alzheimer-type dementia, and many drugs have been attempted for treating Alzheimer-type dementia but there are no drug proving its significant effects. Only acetylcholinesterase inhibitor which acts in acetylcholine, is used as a treating agent, but it is known that it partially exhibits an improvement of a cognitive function but does absolutely no action in proceeding of Alzheimer's disease. And thus, there is a need for a development of the effective agent for preventing or treating dementia.

Meanwhile, lactic acid bacteria have been used for a long time and their intestinal regulations, anticancer effects, immune boost effects and the like have been reported. Therefore, inventors of the present invention had been studied for searching lactic acid bacteria having beneficial effects in aging and dementia, and as a result, confirmed that novel lactic acid bacteria isolated from Kimchi have effects for preventing or treating aging and dementia and then completed the present invention.

SUMMARY

An object of the present invention is to provide lactic acid bacteria having effects for preventing or treating an aging and dementia.

In addition, another object of the present invention is to provide an antioxidant and anti-aging composition and a composition for preventing or treating dementia, which include the lactic acid bacteria.

Furthermore, still another object of the present invention is to provide an antioxidant and anti-aging fermentation composition, and a fermentation composition for preventing or treating dementia, which are fermented with the lactic acid bacteria.

To achieve said objects, the present invention provides *Lactobacillus pentosus* var. *plantarum* C29 KCCM11291P isolated from Kimchi.

In addition, the present invention provides an antioxidant and anti-aging pharmaceutical composition including *Lactobacillus pentosus* var. *plantarum* C29 as an active ingredient.

In addition, the present invention provides a pharmaceutical composition for preventing or treating dementia, which includes *Lactobacillus pentosus* var. *plantarum* C29 as an active ingredient.

In addition, the present invention provides a health dietary supplement having antioxidant and anti-aging effects, which includes *Lactobacillus pentosus* var. *plantarum* C29 as an active ingredient.

In addition, the present invention provides a health dietary supplement for preventing or improving dementia, which includes *Lactobacillus pentosus* var. *plantarum* C29 as an active ingredient.

In addition, the present invention provides an antioxidant and anti-aging composition including a fermentation composition, which is fermented with *Lactobacillus pentosus* var. *plantarum* C29, as an active ingredient.

In addition, the present invention provides a composition for preventing or treating dementia, which includes a fermentation composition that is fermented with *Lactobacillus pentosus* var. *plantarum* C29, as an active ingredient.

In addition, the present invention provides *Lactobacillus curvatus* C3 KCCM43009 isolated from Kimchi.

In addition, the present invention provides an antioxidant and anti-aging pharmaceutical composition including *Lactobacillus curvatus* C3 as an active ingredient.

In addition, the present invention provides a pharmaceutical composition for preventing or treating dementia, which includes *Lactobacillus curvatus* C3, as an active ingredient.

In addition, the present invention provides a health dietary supplement having antioxidant and anti-aging effects, which includes *Lactobacillus curvatus* C3, as an active ingredient.

In addition, the present invention provides a health dietary supplement for preventing or improving dementia, which includes *Lactobacillus curvatus* C3, as an active ingredient.

In addition, the present invention provides an antioxidant and anti-aging composition including a fermentation composition, which is fermented with *Lactobacillus curvatus* C3, as an active ingredient.

In addition, the present invention provides a composition for preventing or treating dementia, which includes a fermentation composition that is fermented by *Lactobacillus curvatus* C3, as an active ingredient.

BRIEF DESCRIPTION OF DRAWINGS

FIG. 1 illustrates the 16S rDNA sequence of C29 lactic acid strain (SEQ ID NO. 1).

$p<0.05$ vs. normal control, *$p<0.05$ vs. scopolamine single treatment control.

Figure 8:
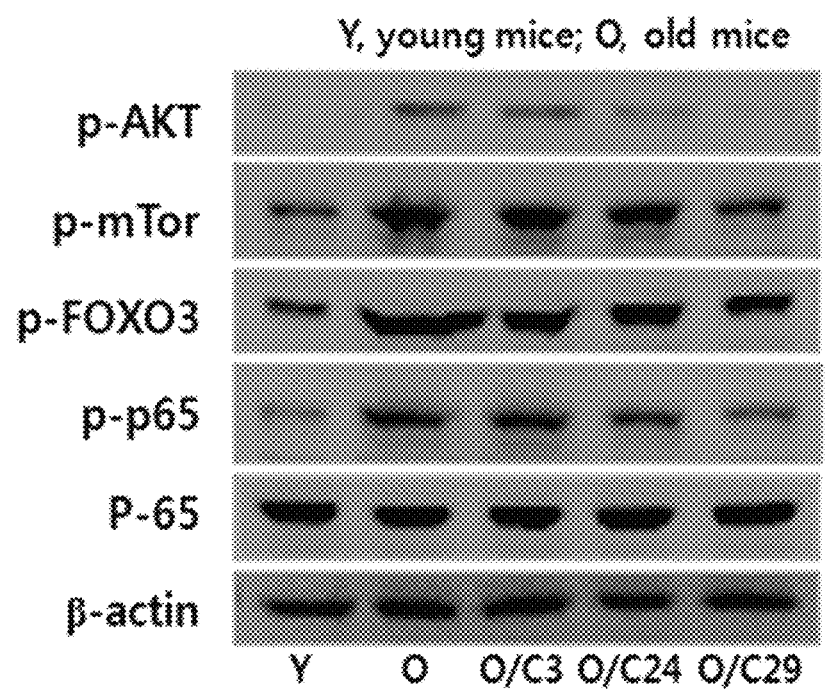

FIG. 8 is a gel photograph illustrating a change in an amount of the expression of aging-associated gene phosphate according to the administration of a C29 strain.

Figure 9:
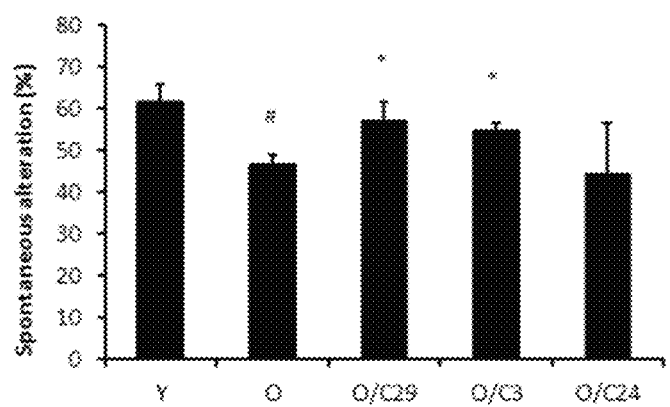

FIG. 9 is a graph illustrating the results of a Y maze task in Example 3, in which Y represents the young mice, O represents the aged mice, O/C29 represents the aged mice administered with C29 lactic acid bacteria ($1\times10^9$ colony forming unit (CFU)/mouse), O/C3 represents the aged mice administered with C3 lactic acid bacteria ($1\times10^9$ colony forming unit (CFU)/mouse), and O/C24 represents the aged mice administered with C24 lactic acid bacteria ($1\times10^9$ colony forming unit (CFU)/mouse).

FIG. 10 is a graph illustrating the results of a water maze task in Example 3, in which Y represents the young mice, O represents the aged mice, O/C29 represents the aged mice administered with C29 lactic acid bacteria ($1\times10^9$ colony forming unit (CFU)/mouse), O/C3 represents the aged mice administered with C3 lactic acid bacteria ($1\times10^9$ colony forming unit (CFU)/mouse), and O/C24 represents the aged mice administered with C24 lactic acid bacteria ($1\times10^9$ colony forming unit (CFU)/mouse). The value is an average±SEM (n=6).

FIG. 11 illustrates 16S rDNA sequence (SEQ ID NO. 2) of C3 lactic acid bacteria.

Figure 12:
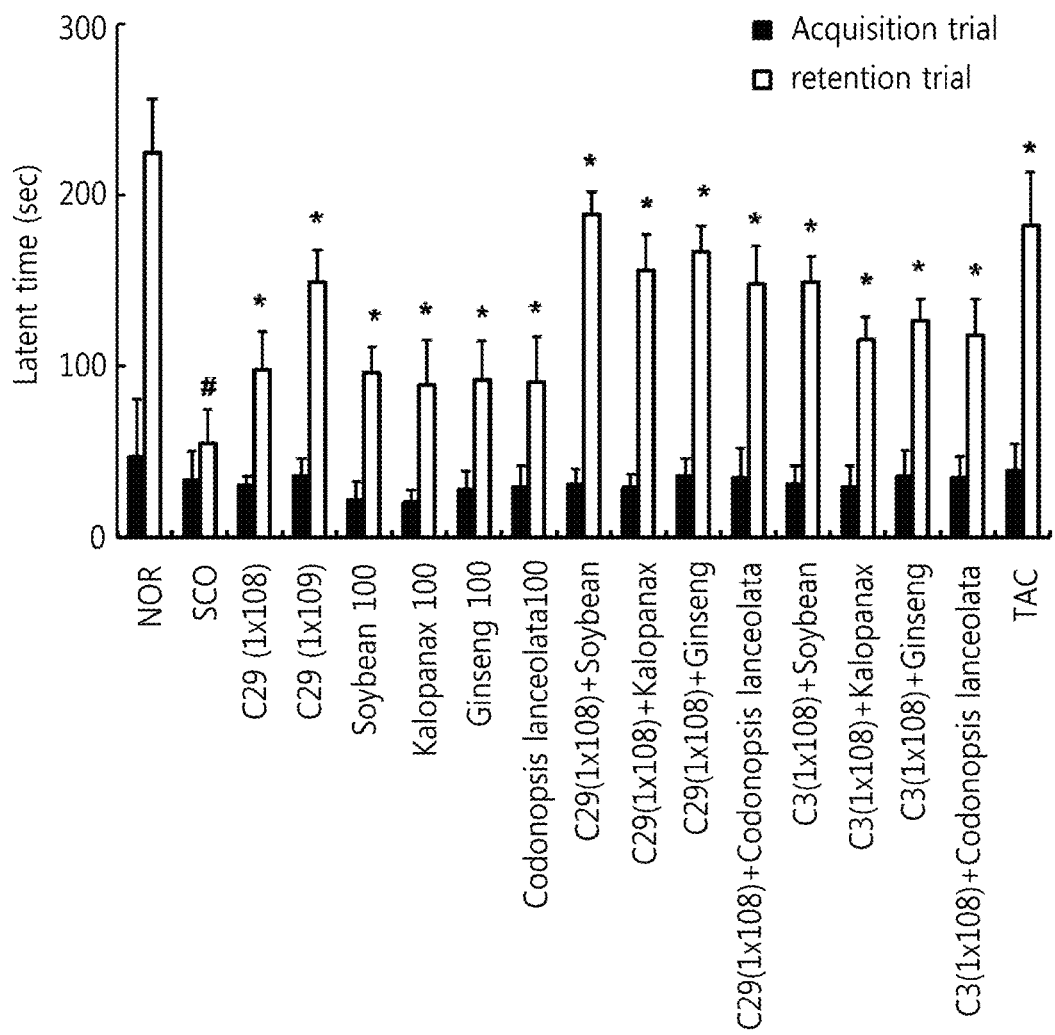

FIG. 12 is a graph illustrating the cognitive function-improvement effect of the fermentation composition fermented by a C29 strain or C3 strain.

DETAILED DESCRIPTION

The *Lactobacillus pentosus* var. *plantarum* C29 and *Lactobacillus curvatus* C3 of the present invention are novel microorganisms isolated from cabbage Kimchi.

The *Lactobacillus pentosus* var. *plantarum* C29 of the present invention is a strain belonging to *lactobacillus* in a molecular phylogenetic systematic and biochemical characteristic analysis based on 16s rDNA base sequence and was identified as the strain exhibiting a high level of the molecular phylogenetic systematic relationship with both of *Lactobacillus pentosus* and *Lactobacillus plantarum*, but since its biochemical characteristics were more similar to those of *Lactobacillus pentosus*, it was called as *Lactobacillus pentosus* var. *plantarum* C29, and deposited, in compliance with the Budapest Treaty on the International Recognition of the Deposit of Microorganisms for the Purpose of Patent Procedure, on the International Depository Authority, Korean Culture Center of Microorganisms ("KCCM") as a Deposit No. KCCM1129P, on Jul. 9, 2012. The deposit was accepted as viable on Apr. 10, 2015. KCCM has an address of 361-221, Yurim B/D, Hongje-1-dong, Seodaemun-gu, SEOUL 120-091, Republic of Korea.

In addition, since the *Lactobacillus curvatus* C3 of the present invention is a strain belonging to *lactobacillus* in the molecular phylogenetic systematic analysis based on 16s rDNA base sequence, and was identified as the strain belonging to *Lactobacillus curvatus*, and thus, it was called as *Lactobacillus curvatus* C3, and deposited on the International Depository Authority, KCCM as a Deposit No. KCCM43009, on Jul. 9, 2012.

The *Lactobacillus pentosus* var. *plantarum* C29 (hereinafter, also referred to as "C29") and the *Lactobacillus curvatus* C3 (hereinafter, also referred to as "C3") of the present invention were identified as having effects on improving a memory of mice by a passive avoidance response test using an animal model, mouse with Alzheimer's disease when the C29 strain or C3 strain is administered, and the C29 strain was also identified as having the memory improvement effect even in a Y maze task and a water maze task, and thus, these effects on preventing and treating dementia were confirmed (See Example 2).

For the present invention, dementia refers to the state, in which a brain function is damaged by various reasons, and also a cognitive function such as a memory, linguistic skills, and judgments is consistently and generally lowered than ever before thereby exhibiting the negative effects in the daily life, and includes senile dementia, Alzheimer's disease, vascular dementia, Lewy body dementia, frontotemporal dementia, Parkinson's dementia, Huntington's dementia, dementia induced by normal pressure hydrocephalus, dementia induced by a head injury, dementia induced by a material, and the like.

In addition, as the results of measuring lipid peroxides, superoxide dismutase activity, catalase activity, and glutathione concentration after administering the C29 strain or C3 strain to the mice aged 16 months for 3 months, the significant superior antioxidant effects were exhibited as compared with the mice aged 16 months administered with physiological saline for 3 months, and the decreases of the expressions of the aging-associated genes were exhibited, and thus, the antioxidant and anti-aging effects were confirmed (see Table 6 and Example 3).

Therefore, the *Lactobacillus pentosus* var. *plantarum* C29 and *Lactobacillus curvatus* C3 of the present invention were identified as being strains having superior effects for preventing and treating dementia and an aging.

The morphological features, the physiological features, the analysis results of the sucrose fermentation, and the composition of cellular fatty acid of the *Lactobacillus pentosus* var. *plantarum* C29 of the present invention are listed with the features of the known *L. plantarium* ATCC 14917 and *L. pentosus* DSM20314, in the following Tables 1, 2 and 3.

TABLE 1

Morphological and physiological features of strains C29, *L. plantarum* ATCC 14917 and *L. pentosus* DSM20314

| Feature | Strain C29 | *L. plantarum* ATCC 14917 ™ | *L. pentosus* DSM20314 ™ |
|---|---|---|---|
| Morphological feature | | | |
| Shape of cell | Rod | Rod | Rod |
| Gram-stain | Positive | Positive | Positive |
| Size of cell (μm) | 1-1.2 × 2.2-2.6 | 0.4-0.6 × 0.8-2 | 0.8-1 × 2-6 |
| Physiological feature | | | |
| Generation of indol | − | − | − |
| Gas generation of glucose | − | − | − |
| Catalase | − | − | − |
| Oxidase | − | − | − |
| Growth in MRS medium | | | |
| 10° C. | + | + | + |
| 15° C. | + | + | + |
| 45° C. | + | − | − |
| Growth at various pHs | | | |
| pH 3 | + | − | − |
| pH 5 | + | + | + |
| pH 7 | + | + | + |
| Growth under the presence of NaCl | | | |
| 6% | + | + | + |
| 8% | + | + | + |
| 10% | − | − | − |
| Stability in gastric juice | Stable | Unstable | Unstable |
| Stability in intestinal juice | Stable | Unstable | Unstable |
| G + C (mol %) | 50.7 | 44.1[a] | 46.1[a] |

+: positive response;
−: negative response
[a]commercially available from Zanoni, P., Farrow, J. A. E. Philips, B. A., Collins, M. D. (1987) *Lactobacillus pentosus* (fred, peterson, and anderson) sp. Nov., norn, rev. Int J Syst Bacteriol 37, 339-341.

TABLE 2

Analysis of sucrose fermentation of lactic acid bacteria using API 20E and API 50CHL

| | Strain C29 | *L. plantarum*[a] ATCC14917 ™ | *L. pentosus*[b] DSM20314 ™ |
|---|---|---|---|
| API 20E | | | |
| ONPG | − | − | − |
| TDA | − | − | − |
| IND | − | − | − |
| ADH | − | − | − |

TABLE 2-continued

Analysis of sucrose fermentation of lactic acid bacteria using API 20E and API 50CHL

| | Strain C29 | *L. plantarum*[a] ATCC14917 ™ | *L. pentosus*[b] DSM20314 ™ |
|---|---|---|---|
| LDC | − | − | − |
| ODC | − | − | − |
| URE | − | − | − |
| H₂S | − | − | − |
| VP | + | + | + |
| API 50CHL | | | |
| Glycerol | − | − | + |
| L-arabinose | + | + | + |
| D-ribose | + | + | + |
| D-xylose | − | − | + |
| Adonitol | − | − | − |
| D-galactose | + | + | + |
| D-glucose | + | + | + |
| D-fructose | + | + | + |
| D-manose | + | + | + |
| L-rhamnose | + | − | D |
| Dulcitol | − | − | D |
| Manitol | + | + | + |
| Sorbitol | + | + | + |
| α-methyl-D-mannoside | + | + | − |
| α-methyl-D-glucoside | − | − | D |
| N-acetyl-glucosamine | + | + | + |
| Amygdaline | + | + | + |
| Arbutin | + | + | + |
| Esculin | + | + | + |
| Salicine | + | + | + |
| Cellobiose | + | + | + |
| Maltose | + | + | + |
| Lactose | + | + | + |
| Melibiose | + | + | + |
| Sucrose | + | + | + |
| Trehalose | + | + | + |
| Inuline | + | − | − |
| Melezitose | + | + | D |
| Rapinose | + | + | + |
| Gentiobiose | + | + | + |
| D-turanose | + | + | D |
| D-arabitol | − | + | D |
| Gluconate | + | − | + |

+: positive response;
−: negative response;
D: variable response
[a]commercially available from Van Reenen, C. A., Dicks, L. M. (1996) Evaluation of numerical analysis of random amplified polymorphic DNA (rapd)-per as a method to differentiate *lactobacillus plantarum* and *lactobacillus pentosus*. Curr Microbiol 32, 183-187.
[b]commercially available from Zanoni, P., Farrow, J. A. E., Phillips, B. A., Collins, M. D. (1987) *Lactobacillus pentosus* (fred, peterson, and anderson) sp. Nov., norn, rev. Int J Syst Bacteriol 37, 339-341.

Any one of the above three lactic acid bacteria did not ferment 2-keto-gluconate, 5-keto-gluconate, erythritol, D-arabinose, L-xylose, β-methyl-D-xyloside, L-sorbose, inositol, glycogen, xylitol, D-lyxose, D-tagatose, D-fucose, L-fucose, and L-arabitol.

TABLE 3

Compositions of cellular fatty acid of strains C29, *L. plantarum* ATCC 14917 and *L. pentosus* DSM20314

| Fatty acid | Strain C29 | *L. plantarum*[a] ATCC14917 ™ | *L. pentosusa* DSM20314TM |
|---|---|---|---|
| Saturated fatty acid | | | |
| $C_{12:0}$ | 1.1 | T | T |
| $C_{14:0}$ | 3.9 | 4.1 | 3.9 |
| $C_{16:0}$ | 45.5 | 34.1 | 20.8 |
| $C_{18:0}$ | 5.0 | 3.3 | 4.3 |

TABLE 3-continued

Compositions of cellular fatty acid of strains C29,
L. plantarum ATCC 14917 and L. pentosus DSM20314

| Fatty acid | Strain C29 | L. plantarum[a] ATCC14917 ™ | L. pentosusa DSM20314TM |
|---|---|---|---|
| Unsaturated fatty acid | | | |
| $C_{16:1}$ ω7c | 8.7 | 3.9 | 5.6 |
| $C_{18:1}$ ω7c | 25.5 | 27.2 | 45.1 |
| Branched fatty acid | | | |
| $C_{19:0}$ cyclo ω8c | 10.1 | 8.7 | 5.7 |

T: less than 1% of a trace of acid
[a]L. plantarum: commercially available from Van Reenen, C. A., Dicks, L. M. (1996) Evaluation of numerical analysis of random amplified polymorphic DNA (rapd)-per as a method to differentiate lactobacillus plantarum and lactobacillus pentosus. Curr Microbiol 32, 183-187.
L. pentosus: commercially available from Zanoni, P., Farrow, J. A. E., Phillips, B. A., Collins, M. D. (1987) Lactobacillus pentosus (fred, peterson, and anderson) sp. Nov., norn, rev. Int J Syst Bacteriol 37, 339-341.

Also, the morphological features, the physiological features, and the results of fermentation of sucrose of the *Lactobacillus curvatus* C3 of the present invention are listed along with the features of the known *L. curvatus* ATCC25601 in the following Tables 4 and 5.

TABLE 4

Morphological and physiological features
of strains C3 and L. curvatus ATCC 25601

| Feature | Strain C3 | L. curvatus ATCC25601 |
|---|---|---|
| Morphological feature | | |
| Shape of cell | Rod | Rod |
| Gram-stain | Positive | Positive |
| Size of the cell (μm) | 1-1.2 × 2.2-2.6 | 0.4-0.6 × 0.8-2 |
| Physiological feature | | |
| Generation of indol | − | − |
| Gas generation of glucose | − | − |
| Catalase | − | − |
| Oxidase | − | − |
| Growth in MRS medium | | |
| 10° C. | + | + |
| 15° C. | + | + |
| 45° C. | − | − |
| Growth at various pHs | | |
| pH 3 | − | − |
| pH 5 | + | + |
| pH 7 | + | + |
| G + C (mol %) | 41.9 | |

+: positive response;
−: negative response

TABLE 5

Analysis of sucrose fermentation of lactic acid
bacteria using API 20E and API 50CHL

| | Strain C3 | L. curvatus ATCC25601 |
|---|---|---|
| API 20E | | |
| $H_2S$ | − | − |
| VP | + | + |
| API 50CHL | | |
| L-arabinose | − | − |
| D-ribose | + | + |
| D-xylose | − | − |
| D-galactose | + | + |
| D-glucose | + | + |
| D-fructose | + | + |
| D-mannose | + | + |
| L-rhamnose | + | + |
| Sorbitol | − | − |
| amygdalin | − | − |
| esculin | + | + |
| salicine | + | + |
| Cellobiose | + | + |
| maltose | + | + |
| lactose | + | + |
| melibiose | − | − |
| sucrose | − | − |
| trehalose | − | − |
| melezitose | − | − |
| rapinose | − | − |

+: positive response;
−: negative response;

Any one of the above three lactic acid bacteria did not ferment 2-keto-gluconate, 5-keto-gluconate, erythritol, D-arabinose, L-xylose, β-methyl-D-xyloside, L-sorbose, inositol, glycogen, xylitol, D-lyxose, D-tagatose, D-fucose, L-fucose, and L-arabitol.

The *Lactobacillus pentosus* var. *plantarum* C29 strain and *Lactobacillus curvatus* C3 strain of the present invention may be used for preventing and treating aging and dementia, and thus, the present invention provides an antioxidant and anti-aging pharmaceutical composition and a pharmaceutical composition for preventing or treating dementia, which include a *Lactobacillus pentosus* var. *plantarum* C29 strain or a *Lactobacillus curvatus* C3 strain as an active ingredient.

The pharmaceutical composition of the present invention may be administered orally (e.g., taking medicine by mouth or inhalation) or parenterally (e.g., injection, percutaneous absorption, or rectal administration), and the injection may be, for example, a venous injection, a subcutaneous injection, an intramuscular injection, or an intraperitoneal injection. The pharmaceutical composition according to the present invention may be formulated into a tablet, capsule, granule, fine subtilae, powder, sublingual tablet, suppository, ointment, injection, turbid liquid, suspension, syrup, spray, and the like, according to an administration route. The pharmaceutical compositions according to the present invention in the above-described various forms may be prepared by the known techniques using a pharmaceutical acceptable carrier that is generally used for each of the formulations. Examples of the pharmaceutical acceptable carrier include an excipient, binding agent, disintegrating agent, lubricant, preservative, antioxidant, isotonic agent, buffer, coating agent, sweetening agent, solubilizer, base, dispersion, wetting agent, suspending agent, stabilizer, colorant, and the like.

The pharmaceutical composition according to the present invention includes the *Lactobacillus pentosus* var. *plantarum* C29 strain or *Lactobacillus curvatus* C3 strain of the present invention in the amount of about 0.01 to 100 wt %, depending on their pharmaceutical formulations.

The specific dose of the pharmaceutical composition of the present invention may be varied according to a kind, a body weight, a sex, a degree of the disease of a mammal including a human to be treated, a decision of a practitioner, and the like, and the proper dose according to the specific use may be determined by the person ordinary skilled in the art. Preferably, for an oral administration, 0.001 to 500 mg of an active ingredient per 1 kg of a body weight per a day is administered, and for a parenteral administration, 0.01 to 200 mg of an active ingredient per 1 kg of a body weight per a day is administered. More preferably, 100 mg of an active ingredient per 1 kg of a body weight per a day is administered. The total dose per a day may be administered at one time or several times depending on a degree of a disease, a judgment by a practitioner and the like.

The present invention also provides a health dietary supplement having an antioxidant and anti-aging effects and a health dietary supplement for preventing or improving dementia, which includes a C29 strain or a C3 strain as an active ingredient.

A kind of the health dietary supplement of the present invention is not specifically limited, and the health dietary supplement of the present invention may be in a form of an oral-type formulation, such as, a powder, granule, table, capsule, suspension, emulsion, and syrup, or may be added to a general food, such as, a candy, cracker, gum, ice cream, noodle, bread, and beverage.

The health dietary supplement of the present invention may be prepared by properly using a filler, extender, binder, wetting agent, disintegrating agent, sweetening agent, flavoring agent, preservative, surfactant, lubricant, excipient, and the like in a routine manner according to its forms.

The content of a C29 strain or C3 strain for the preparation of the above-described health dietary supplement is different according to a form of a health dietary supplement, but the content thereof may be approximately 0.01 to 100 wt %.

In addition, the present invention provides a composition having an antioxidant and anti-aging effect and a composition for preventing or improving dementia, which include a fermentation composition that is fermented with a C29 strain or C3 strain, as an active ingredient.

In the present invention, the fermentation composition includes a fermentation composition of a soybean or defatted soybean, a fermentation composition of *kalopanax*, a fermentation composition of *ginseng*, and a fermentation composition of *Codonopsis lanceolata*.

In the present invention, a water suspension of the powder of the soybean or defatted soybean means to one prepared by adding 5 to 15 times water to the powder's weight to the powder of the dried soybean or defatted soybean and suspending the powder in the water, but the present invention is not limited thereto. A type of soybean milk prepared by grinding the soybean soaked in water may be used, as long as it corresponds to the objects of the present invention.

In the present invention, the *kalopanax, ginseng* and *Codonopsis lanceolata* may be in a form of an extract or essence, and preferably, a type of the extract prepared by a hydrothermal extraction, ethyl alcohol extraction or mixed extraction may be used, but the present invention is not limited thereto. In order to increase the extraction efficiency of the above-described extract, it may be ground or powdered, and the grinding and pulverization process may be conducted according to the conventional extraction method well-known in the art. For example, a water extraction method, alcohol extraction method, organic solvent extraction method and supercritical extraction method, and the like, may be used, and preferably the water extraction method is used, but the present invention is not limited thereto.

As an extraction solvent used in the above-described alcohol extraction method, low alcohol having 1 to 6 carbon atoms, and the like, such as methanol, ethanol, propanol, isopropanol, and butanol, may be used, and as an extraction solvent used in the above-described organic solvent extraction method, an organic solvent such as acetone, ether, benzene, chloroform, ethylacetate, methylene chloride, hexane, hydrochloric acid, acetic acid, formic acid, citric acid, cyclohexane and petroleum ether; or a mixture thereof may be used.

At this time, the rate of the extraction solvent added at the time of extraction is not specifically limited, but 2 to 20 times (based on the weight) of the extraction solvent with respect to the dry weight of *kalopanax, ginseng*, or *Codonopsis lanceolata* may be used. In order to increase the extraction efficiency, preferably, the extraction may be repeated several times, for example, 2 times or more by using 5 times to 15 times (based on the weight) of the extraction solvent with respect to *kalopanax, ginseng* or *Codonopsis lanceolata*.

At this time, an extraction temperature is preferably 50 to 110° C., and more preferably, 70 to 100° C. An extraction time varies according to the extraction temperature, but may be 1 to 48 hours, and preferably 2 to 8 hours. In addition, when it is stirred with a shaker at the time of extraction, the extraction efficiency may be more increased.

The extract may be prepared by a decompression distillation method or thin film distillation method.

In the present invention, the effects of the soybean or defatted soybean fermentation composition fermented by inoculating a C29 strain or C3 strain, the *kalopanax* fermentation composition, the *ginseng* fermentation composition, and the *Codonopsis lanceolata* fermentation composition on improving the memories of mice are confirmed in a passive avoidance response task by using the mice, an animal model with Alzheimer's disease, and thus, the effects for preventing or treating dementia are confirmed (see Example 5).

In the present invention, when the C29 strain or C3 strain is inoculated on the above-described extract, the extract is used after heating the extract at the temperature of 100° C. or more for 15 minute to 1 hour for a sterilization to inhibit the growth of spoilage bacteria at the time of the inoculation.

Although the inoculating amount of the C29 strain or C3 strain varies according a kind of the extract used in the fermentation, the inoculating amount thereof is to be $1 \times 10^8$ CFU/ml or more and a fermentation temperature is preferably 20 to 40° C. Although a fermentation time is not specifically limited as long as it corresponds to the objects of the present invention, the fermentation time may be 10 to 30 hours after inoculating the C29 strain or C3 strain. In this case, when it is fermented for 10 hours or more, the fermentation composition is not sufficiently made, and when it is fermented for 30 hours and more, an organic acid is made much so as to generate strong sour taste and thus decrease a mouthfeel, and therefore, it is preferable to ferment it within the range of the fermentation time as mentioned above.

In addition, in the present invention, various fermentation food may be prepared according to the materials used in the fermentation; and for example, a fermentation beverage of lactic acid bacteria such as a yogurt may be prepared by inoculating a C29 strain or C3 strain to dry milk or milk, and then, fermenting it by the manner as above.

Advantageous Effects

It is confirmed that the *Lactobacillus pentosus* var. *plantarum* C29 strain or *Lactobacillus curvatus* C3 strain of the present invention has the superior effects on preventing and improving aging and dementia, and thus, they can be usefully utilized in the prevention or treatment of aging and dementia. Therefore, the pharmaceutical composition and the health dietary supplement including the *Lactobacillus pentosus* var. *plantarum* C29 strain or *Lactobacillus curvatus* C3 strain of the present invention can be effectively used for preventing or treating aging and dementia. Since the strains which are present in Kimchi intaken routinely are an active ingredient, it can be used without any concern for side effects or toxicity. In addition, since the fermentation compositions are prepared by inoculating the *Lactobacillus pentosus* var. *plantarum* C29 strain or *Lactobacillus curvatus* C3 strain of the present invention, they can be effectively utilized as the compositions for preventing or treating aging and dementia.

EXAMPLES

Hereinafter, the present invention will be described in more detail with reference to Examples. These Examples are only to illustrate the invention, and it is self-evident to the skilled person in the art that the scope of the present invention is not to be limited to such Examples.

Example 1

Isolation of Lactic Acid Bacteria

Cabbage Kimchi was suspended in MRS broth, the supernatant thereof was inoculated on MRS agar medium, and then, the medium thereof was anaerobically cultured at a temperature of 37° C. for 24 hours. Since then, the colony being grown out was selected and gram-stained, and 16S rDNA thereof was analyzed, and then a *lactobacillus* strain was isolated.

In addition, human feces were suspended in GAM broth (Nissui Pharmaceutical Company, Ltd., Japan), the supernatant thereof was inoculated on BL agar medium (Nissui Pharmaceutical) and then, the medium thereof was anaerobically cultured at 37° C. for 48 hours. Since then, the colony being grown out was selected and gram-stained, and 16S rDNA thereof was analyzed, and then, the *lactobacillus* and *Bifidobacterium* strains were isolated.

The isolated strains are as follows:
1) Lactic acid bacteria used by isolating from Kimchi
*Leuconostoc mesenteroides* C1
*Leuconostoc kimchii* C2
*Lactobacillus curvatus* C3
*Lactobacillus brevis* C4
*Lactobacillus brevis* C5
*Lactococcus plantarum* C6
*Leuconostoc citreum* C7
*Pediococcus pentosus* C8
*Lactobacillus acidophilus* C9
*Lactobacillus lactis* C10
*Lactobacillus helveticus* C11
*Lactobacillus plantarum* C12
*Lactobacillus casei* C13
*Lactobacillus sakei* C14
*Lactobacillus pentosus* C15
*Lactobacillus sakei* C21
*Lactobacillus sakei* C22
*Lactobacillus sakei* C23
*Lactobacillus plantarum* C24
*Lactobacillus plantarum* C25
*Lactobacillus plantarum* C26
*Lactobacillus pentosus* C27
*Lactobacillus pentosus* C28
*Lactobacillus pentosus* var. *plantarum* C29
*Lactobacillus sakei* C30

2) Lactic acid bacteria used by isolating from human digestive tract
*Bifidobacterium breve* C16
*Bifidobacterium longum* C17
*Bifidobacterium adolescentis* C18
*Bifidobacterium bifidum* C19
*Latobacillus acidophilus* C20

Example 2

Identification of Anti-Dementia Effects

In order to identify lactic acid bacteria having anti-dementia effects among 30 lactic acid bacteria isolated from Kimchi and feces, an experiment was performed by using the above-described C1 to C30 strains and laboratory animals.

All animals used in the experiment were the male ICR-based mice (28 to 30 g), and the experiment was performed in accordance with Guide for the Care and Use of Laboratory Animal (NIH publication No. 85-23). 5 and 6 laboratory animals were housed in a cage and were leaved to freely access to the food. The temperature in the cage was $23\pm1°$ C., the moisture was $60\pm10\%$, and 12 hours of day and night (07:30~19:30) were always maintained.

2-1. Passive Avoidance Task Test

An experimental box (50×15×40 cm, electrofiable frid floor) as an experimental equipment was divided into two sections by using a partition, and it is designed so that when entering one side into the opposite side via a small entrance, the entrance was closed automatically. When an animal was put into one side of the section divided by the partition with turning on the light, it looked around followed entering into the dark section without any light, the entrance was automatically closed, immediately foot shock was made by flowing 0.25 mA of an electric current through stainless grid of a floor for one second. At the next day, the latency from the time that the laboratory animal was put into the section turning on the light to the time that the animal was passed over the dark section and then the entrance was closed was determined. The latencies until the mouse enters into the dark section like this were determined and compared for the control and test groups. The maximal limitation time was set to 300 seconds, wherein if the mouse did not enter into the dark section until over 300 seconds, the passive avoidance response latency was determined as 300 seconds. It was determined that greater the time until the animal passes over the dark section and the entrance was closed, the memory for passive avoidance through learning was well remained.

Figure 2:
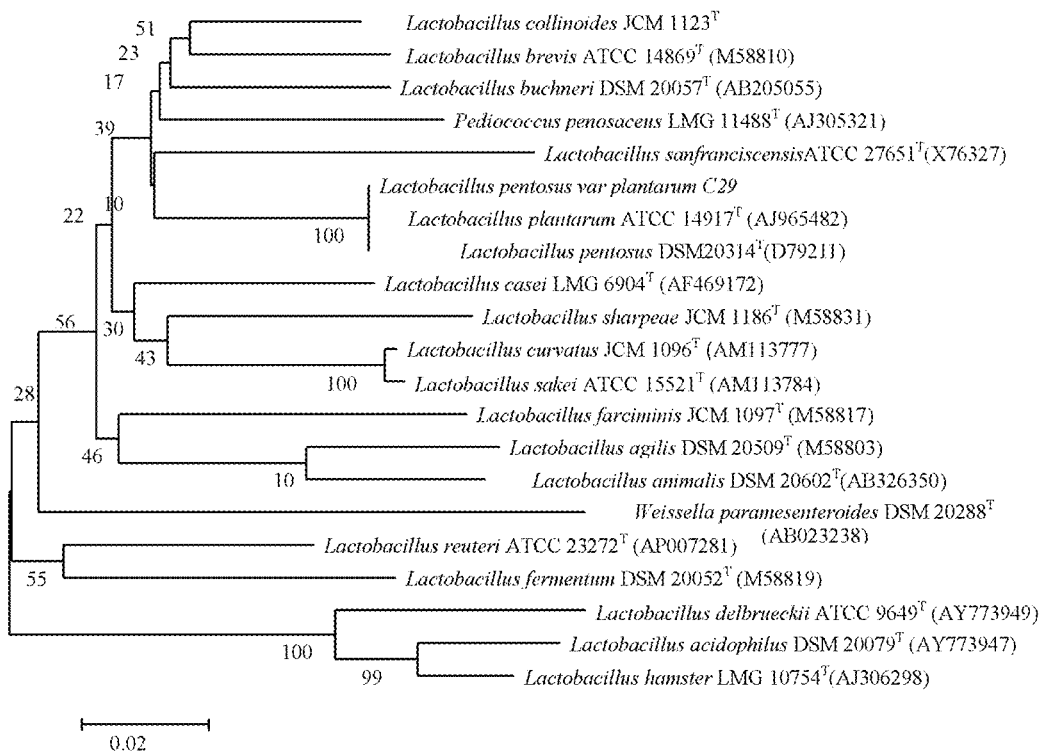
FIG. 2 is a phylogenetic tree illustrating a position of *Lactobacillus pentosus* var. *plantarum* C29.
Figure 3:
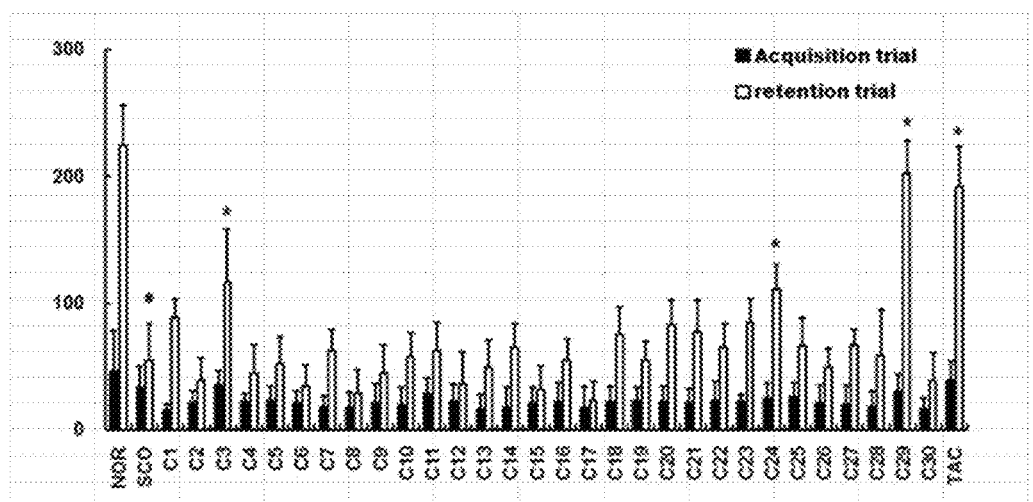
FIG. 3 is a graph illustrating the results of a passive avoidance response task.

30 kinds of C1 to C30 lactic acid bacteria used in the experiment were administered to the animal model with dementia in a number of $1\times10^{10}$ CFU one per 1 day for 2 days. Scopolamine (0.9 mg/kg) was administered at 1 hour after the last administration of lactic acid bacteria. As a result, as can be identified in FIG. 3, C29 of lactic acid bacteria used in the experiment best maintained the memory for the passive avoidance and exhibited the effects superior to Tacrin (TAC, 10 mg/kg), the treating agent of dementia, and it was the order of C3, and then C24.

Figure 4:
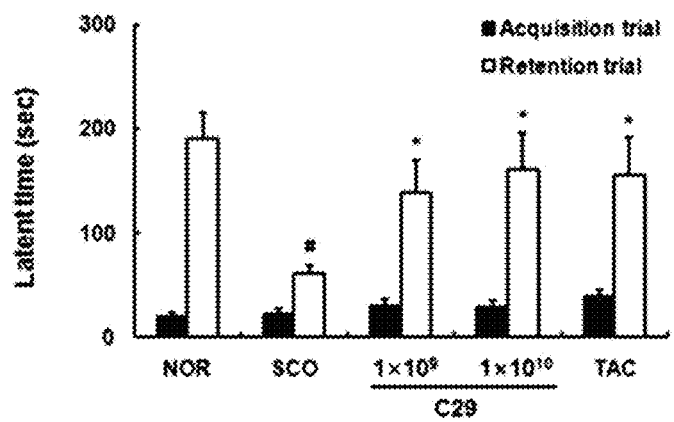
FIG. 4 is a graph illustrating the effect of a C29 strain on improving memory that is increased in a concentration-dependent manner.

C29 lactic acid bacteria identified as having the best effects were administered to the mouse in $1\times10^9$ and $1\times10^{10}$ CFU one per 1 day for two (2) days. Scopolamine (0.9 mg/kg) was administered at one hour after the last administration of lactic acid bacteria. As a result, as identified in FIG. 4, C29 exhibited the effects in a concentration-dependent manner.

In addition, in order to identify the effect for improving dementia in the animal, hippocampus of a brain was isolated and was homogenized by adding 100 μg of RIPA buffer (Gibco) with protease inhibitor cocktail. After centrifuging it at 4° C., 13000 rpm for 15 minutes, p-CREB, CREB, BDNF and β-actin were measured by an immunoblotting method, while the supernatant was stored at −80° C.

Figure 5:
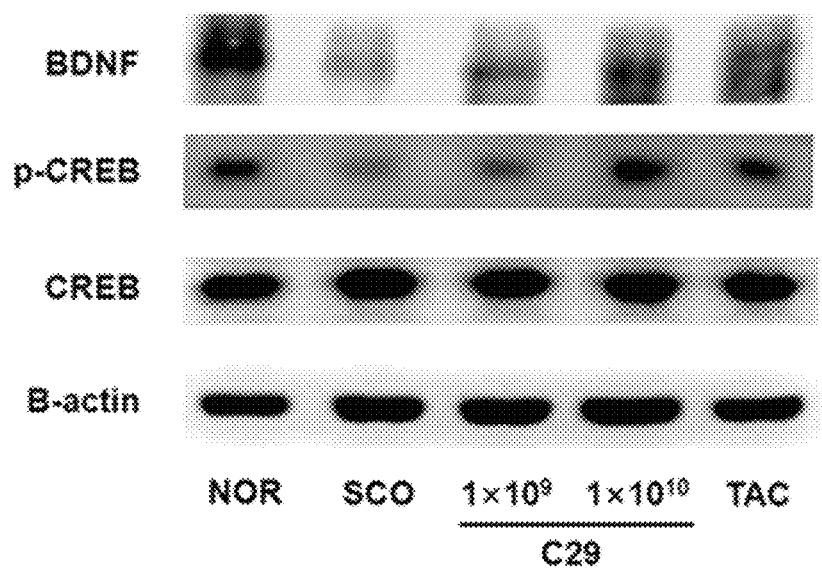
FIG. 5 is a gel photograph illustrating the effect of a C29 strain on improving memory.

Firstly, the supernatant was taken and subjected to an electrophoresis on SDS 10% (w/v) polyacrylamide gel for an hour and a half (sample, 50 μg). The gel subjected to electrophoresis was transferred onto a nitrocellulose paper at 100 V, 400 mA for 1 hour and 10 minutes, the transferred nitrocellulose paper was blocked by 5% defatted milk for 30 minutes and then washed with PBS-Tween three times each of 5 minutes, was reacted with the first antibody (Santa Cruz Biotechnology, USA) as 1:100 overnight. And then, after washing it three times with each of 10 minutes, the secondly antibody (Santa Cruz Biotechnology, USA) was reacted as 1:1000 for 1 hour and 20 minutes. And then, it was washed three times for 15 minutes, and was developed by emitting fluorescence. As a result, as can be confirmed in FIG. 5, it could be determined that p-CREB and BDNF which were reduced by only the administration of scopolamine were recovered in the group administered by C29 simultaneously with scopolamine as compared with the animal groups of models with dementia administered by only scopolamine. This fact shows that C29 lactic acid bacteria have the memory improvement effect.

The experimental results as above described show that the C29 and C3 lactic acid bacteria exhibit the dementia improvement effect via an improvement of the memory.

2-2. Y-Maze Task

A Y-maze task measuring equipment had a shape of alphabet Y extending three arms, in which all the branches had 25 cm of a length, 14 cm of a height, and 5 cm of a width, and were positioned in the same angle. A head part of the laboratory animal is headed for the end of a path of Y-maze and let it go around a passage freely for 8 minutes. After recording a movement of the animal, if hind legs of the animal entered the passage, it is considered that the animal is arm entry. The movement of the animal is represented by an alternation, which is defined that if the animal passes three (3) passages continuously, it is defined as being one alternation. An amount of a spontaneous alternation is represented by a percent of the real alternation and the maximal possible alternation (i.e., a value obtained by deducting 2 from the total alternation).

The C29 which is the best one of lactic acid bacteria used in the experiments was administered to the mouse in $1 \times 10^9$ and $1 \times 10^{10}$ CFU one per 1 day for two (2) days. Scopolamine (0.9 mg/kg) was administered at one hour after the last administration of lactic acid bacteria.

Figure 6:
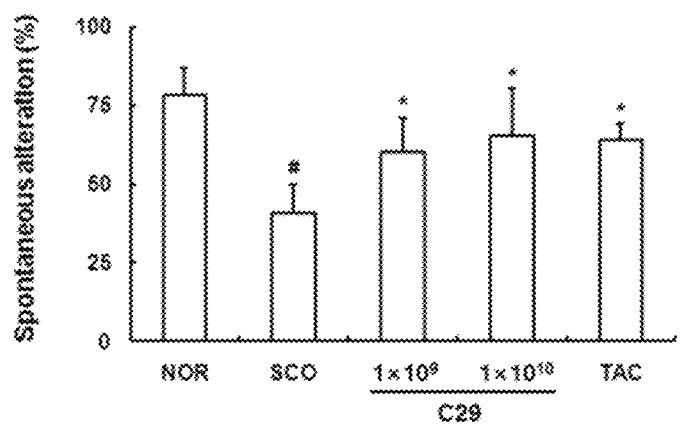
FIG. 6 is a graph illustrating the results of a Y-maze task in Example 2.

As a result, as can be identified in FIG. 6, the test group administered by the C29 exhibited the memory improvement effect in a concentration-dependent manner as compared with the control administered by scopolamine only.

2-3. Water Maze Task

To a circle type of water tank (a diameter of 100 cm and a height of 35 cm), water that was made foggy by putting dry milk so as not to see a platform equipped in water of 23° C. was filled in a depth of 15 cm. In the case of using a mouse, a platform (a diameter of 4.5 cm and a height of 14.5 cm) was placed in the center of one fan shape of 4-divided shapes of water tank so that the top of the platform is placed below 0.5 cm of the surface of water. This device was installed in the laboratory having a mark which can identify the position. A training trial was practiced three times per a day for five days in consequentially. Once the mouse found the platform, it is allowed to stay for 10 sec, and back to the original cage, and after 5 min, the next trial was practiced. If the mouse did not find the platform within 120 sec, it is allowed to stay in the platform for 10 sec, and then finished the trial. A probe test was practiced to the animal that the trial was finished at 24 hrs after the final trial. At this time, the platform was removed from the pool, and the time staying in the 4-divided circle that the platform was placed during 90 sec was measured to represent it as a percentage.

A swimming time was measured daily while administering the best C29 lactic acid bacteria in the amount of $1 \times 10^9$ and $1 \times 10^{10}$ CFU among the lactic acid bacteria used in the experiment once per day for 4 days. Scopolamine (0.9 mg/kg) was administered at 1 hour after the first administration.

Figure 7:
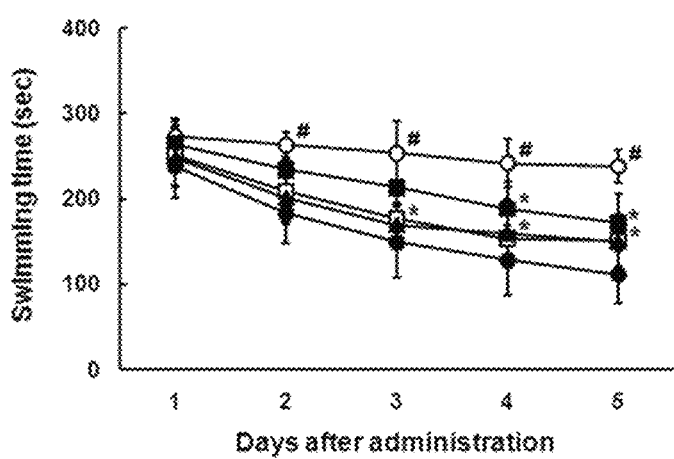
FIG. 7 is a graph illustrating the result of a water maze task in Example 2, in which a black square represents scopolamine+($1\times10^9$ colony forming unit (CFU)/mouse C29), a white square represents scopolamine+($1\times10^{10}$ colony forming unit (CFU)/mouse C29), a black triangle represents scopolamine+(10 mg/kg of tacrine positive control drug), a white circle represents only scopolamine, and a black circle represents the normal control mice. The value is an average±SEM (n=6).

As a result, the C29 lactic acid bacteria exhibited the memory improvement effect in a concentration-dependent manner, as can be seen in FIG. 7.

Example 3

Identifications of Anti-Oxidation, Anti-Aging and Anti-Dementia Effect

In order to identify the anti-oxidation, anti-aging and anti-dementia effect, three lactic acid bacteria C29, C3, C24 ($1 \times 10^9$ CFU, respectively) were administered for five days for 12 weeks, and the anti-aging effect of the lactic acid bacteria and aging-associated gene AKT, FOXO3, NF-κB (p65), mTorr phosphate body in a large intestine that the progress of oxidation reaction is fast, were measured. Beta-actin was measured as a comparative gene. Also, the memory improvement effect was measured.

1) Lipid Peroxide Analysis

To 100 mg of the large intestine tissue of the laboratory animal, 250 μl of RIPA buffer containing protease inhibitor cocktail was added to homogenate. Thereafter, it was centrifuged for 15 min at 4° C., 13000 rpm, and then the surfactant was used in the lipid peroxidation analysis while storing −80° C.

The lipid peroxidation degree in the large intestine tissue was analyzed by using TBARS analysis kit (Cayman chem., USA). 100 μl of homogenate of the large intestine tissue was placed in 5 ml of a polypropylene screw-cap centrifugal tube, and then 100 μl of SDS solution was added and shaken lightly. 4 ml of color reagent was added to the tube, and then put into boiling water for 1 hour to stop the reaction. Thereafter, it was centrifuged for 10 min at 4° C., 13000 rpm, and then allowed to stand for 30 min at the room temperature, and measured the absorbance at 540 nm using an ELISA reader. The standard cure was made by using malonaldehyde (MDA) as a standard material, and the amount of MDA produced from this was measured.

2) Superoxide Dismutase (SOD) Activity

The Cu, Zn-SOD activity was measured by using xanthine oxidase-cytochrome C system. 2. 4 ml of 50 Mm potassium phosphate (pH 7.8, containing 0.1 mM EDTA), 0.3 ml of 0.1 mM pericytochrome C, 0.2 ml of 1% deoxycholate, 0.1 ml of 1.5 mM potassium cyanate, 0.3 ml of 0.5 mM xanthine and 20 ml of xanthine oxidase were thoroughly mixed, and the reduction rate of pericytochrome C was measured at 25° C., 550 nm. 1 unit of SOD was defined as the amount to inhibit 50% reduction of cytochrome C.

3) Catalase Activity

To 2 ml of 50 mM phosphate buffer (pH 7.0), 100 μl of an enzyme source was added, and 1 ml of 10 mM $H_2O_2$ solution was added to measure the reduction of the absorbance for 2 min. 1 unit was defined as the amount of the enzyme which decomposes 1 mol $H_2O_2$ for 1 min.

4) Glutathione (GSH)

A GSH concentration was measured by diluting a sample with a phosphate buffer and adding o-phthaldehyde, shaking for 15 min, and measuring the fluorescence at 345 nm of an excitation wavelength and 425 nm of a radiation wavelength.

As the results of four experiments as above, all 3 strains used in the experiments exhibited excellent anti-oxidation and anti-aging results, as listed in the following Table 6. The most excellent stain was C29, and then in the order of C24 and C3.

TABLE 6

| Group | Activity of the enzyme (mol/min/mg) | | | |
| --- | --- | --- | --- | --- |
| | Superoxide dismutase (mol/min/mg) | Catalase (mol/min/mg) | Malon aldehyde (μmol/mg of protein) | Glutathione (μg/mg of protein) |
| Administering physiological saline to mouse aged 2 months (for three months) | 2.8 ± 0.6 | 6.0 ± 0.6 | 2.5 ± 0.9 | 3.9 ± 0.2 |
| Administering physiological saline to mouse aged 16 months (for three months) | 0.9 ± 0.2 | 0.8 ± 0.5 | 9.4 ± 0.2 | 1.9 ± 1.3 |
| Administering C29 to mouse aged 16 months (for three months) | 1.6 ± 0.4 | 4.5 ± 1.0 | 5.2 ± 1.9 | 3.9 ± 0.5 |
| Administering C3 to mouse aged 16 months (for three months) | 1.8 ± 0.3 | 4.2 ± 1.2 | 5.3 ± 1.2 | 2.8 ± 0.9 |
| Administering C24 to mouse aged 16 months (for three months) | 1.9 ± 0.6 | 4.1 ± 1.6 | 4.2 ± 2.1 | 4.0 ± 1.4 |

In addition, to 100 mg of larger intestine tissue of the laboratory animal, 250 μl of RIPA buffer (Gibco) including protease inhibitor cocktail was added to homogenate. It was centrifuged for 15 min at 4° C., 13000 rpm, and then, phosphor-FOXO3, phosphor-p65, p65, phosphor-mTorr, phosphor-AKT and β-actin were measured via an immuno-blotting method while storing the supernatant at −80° C.

The supernatant was taken and subjected to the electrophoresis in a SDS 10% (w/v) polyacrylamide gel for 1 hr and 30 minutes (sample, 50 μg). The gel subjected to the electrophoresis was transferred to a nitrocellulose paper at 100 V, 400 mA for 1 hour and 10 minutes, the transferred nitrocellulose paper was blocked with 5% defatted milk for 30 minutes and then was washed with PBS-Tween three times with each of 5 minutes, reacted with the first antibody (Santa Cruz Biotechnology, USA) at 1:100 overnight, washed three times with each of 10 minutes, and reacted with the secondly antibody (Santa Cruz Biotechnology, USA) at 1:1000 for 1 hour and 20 minutes. After then, it was washed three times with each of 15 minutes, was development with emitting fluorescence.

The cell treated in the same method as the above method, except for treating it with the active ingredient and LPS, was used as a control. As a result, as illustrated in FIG. 8, it could be seen that in the test group treated with the C29 or C3, the expressions of p-p65, p-FOXO3, p-mTor, p-AKT and the like were significantly reduced as compared with the untreated group, and it showed the antioxidant or anti-aging effects by C29 or C3.

5) Y-Maze Task

A Y-maze task equipment has a shape of alphabet Y extending three arms, wherein the each branch has 25 cm of a length, 14 cm of a height, and 5 cm of a width and placed with the same angle. A head part of the laboratory animal is headed for the end of a path of Y-maze and let it go around the path freely for 8 minutes. After recording a movement of the animal, when hind legs of the animal entered the passage, it is considered that the animal is arm entry. The movement of the animal is represented by alternation, which is defined that when the animal passes three (3) passages continuously, it is defined as one alternation. A spontaneous alternation is represented as a percent of the real alternation and the maximal possible alternation (i.e., a value obtained by deducting 2 from the total alternation).

In this task, the C29 lactic acid bacteria, C3 lactic acid bacteria and C24 lactic acid bacteria were administered to the mice aged 16 months in $1\times10^9$ CFU one per 1 day for two (2) days. In this task, since the memory of the aged mice was lower than that of young mice, scopolamine was not administered.

As a result, as can be identified in FIG. 9, the C29 lactic acid bacteria was the best in the memory improvement effect of the aged mouse, and then was in the order of the C3 lactic acid bacteria and C24 lactic acid bacteria.

6) Morris Water Maze Task

To a circle type of water tank (a diameter of 100 cm and a height of 35 cm), water that was made foggy by putting dry milk so as not to see a platform equipped in water of 23° C. was filled in a depth of 15 cm. In the case of using a mouse, a platform (a diameter of 4.5 cm and a height of 14.5 cm) was placed in the center of one fan shape of 4-divided shapes of water tank so that the top of the platform is placed below 0.5 cm of the surface of water. This device was installed in the laboratory having a mark which can identify the position. A training trial was practiced three times per day for five days 6 in consequentially. Once the mouse found the platform, it is allowed to stay for 10 sec, and back to the original cage, and after 5 min next trial was practiced. If the mouse did not find the platform within 120 sec, it is allowed to stay in the platform for 10 sec, and then finished the trial. A probe test was practiced to the animal that the trial was finished at 24 hrs after the final trial. At this time, the platform was removed from the pool, and the time staying in the 4-divided circle that the platform was placed during 90 sec was measured to represent it as a percentage.

A swimming time was measured daily while administering the C29 lactic acid bacteria, C3 lactic acid bacteria and C24 lactic acid bacteria to the mice aged 16 months in the amount of $1\times10^9$ CFU once per a day for 4 days. In this test, since the memory of the aged mice was lower than that of young mice, scopolamine did not administered.

As a result, as can be identified in FIG. 10, the C29 lactic acid bacteria were the best in the memory improvement effect of the aged mouse, and then were in the order of the C3 lactic acid bacteria and C24 lactic acid bacteria.

Example 4

Identifications of C29 and C3 Lactic Acid Bacteria

In order to identify the C29 strain and C3 strain verified as having the superior antioxidant and anti-aging effects and dementia improvement effects in the above tasks, a phylogenetic analysis was performed through the comparison of 16S rDNA gene sequences When the rDNA base sequences were compared with each other using a BLAST similarity search program, and then, was proceeded an alignment of multiple sequences with the 16S rDNA gene sequences of various *lactobacillus* sp. Strains, and their positions were determined in a phylogenetic tree, since the C29 lactic acid bacteria exhibited at least 99.9% of homologe with *Lactobacillus plantarum* strain BIM B-536 and *Lactobacillus pentosus* strain LS3, they were named as *Lactobacillus plantarum* var. *plantarum* C29 and was deposited to the Depositary Authority, Korean Culture Center of Microorganisms ("KCCM") as a Deposit No. KCCM11291P, on Jul. 9, 2012. In addition, since the C3 lactic acid bacteria exhibited at least 99.9% of homologe with *Lactobacillus curvatus*, they were named as *Lactobacillus curvatus* C3, and were deposited to Deposit Authority, Korean Culture Center of Microorganisms (KCCM) as a Deposit No. KCCM43009, on Jul. 9, 2012.

Example 5

Identification of Anti-Dementia Effect of C29 or C3 Strain Fermentation Composition In order to identify the anti-dementia effects of a soybean or defatted soybean fermentation composition fermented with a C29 or C3 strain, a *kalopanax* fermentation composition, a *ginseng* fermentation composition, and a *Codonopsis lanceolata* fermentation composition, a passive avoidance task test using the laboratory animals was performed in the same method as Example 2.

5-1. Preparation of Fermentation Composition 10 g of a powder of the soybean or defatted soybean was suspended in 90 ml of water and sterilized, and 10 ml of the C29 or C3 strain was added in the amount of $1\times10^8$ CFU/0.1 ml thereto, and then, was cultured for 24 hrs.

10 g of each of a water extract of *kalopanax*, a water extract of *ginseng* and a water extract of *Codonopsis lanceolata* was suspended in 90 ml of water and sterilized, and 10 ml of the C29 or C3 strain was added in the amount of $1\times10^8$/0.1 ml, and then, was cultured for 24 hrs.

5-2. Passive Avoidance Task Test 0.1 ml of each of the soybean or defatted soybean fermentation composition, *kalopanax* fermentation composition, *ginseng* fermentation composition and *Codonopsis lanceolata* fermentation composition prepared by said method was added to the dementia model, mice once per 1 day for two (2) days. Scopolamine (0.9 mg/kg) was administered at one hour after the last administration of lactic acid bacteria. As a result, as can be identified in FIG. 12, the soybean fermentation composition fermented by C29 maintained the best in memory for the passive avoidance and exhibited superior effect as compared with the treating agent of dementia, Tacrin (TAC, 10 mg/kg), and followed by the *ginseng* fermentation composition fermented by C29, soybean fermentation composition fermented by C3, and *Codonopsis lanceolata* fermentation composition fermented by C29 in order. It shows that the fermentation composition fermented by the C29 or C3 strain has the memory improvement effect.

The results of the above-described tasks show that the fermentation composition fermented by the C29 or C3 strain exhibits the dementia improvement effect by improving the memory.

The invention claimed is:

1. A composition comprising:
a fermentation product as an active ingredient, wherein the fermentation product comprises *Lactobacillus pentosus* var. *plantarum* C29 strain (deposit number: KCCM11291P) and is obtained by inoculating a specific substrate with *Lactobacillus pentosus* var. *plantarum* C29 strain (deposit number: KCCM11291P) and culturing it for 10 to 30 hours,
wherein the specific substrate is selected from the group consisting of soybean seeds and defatted soybean seeds.

2. The composition of claim 1, further comprising a pharmaceutically acceptable carrier selected from the group consisting of an excipient, a binding agent, a disintegrating agent, a lubricant, a preservative, an antioxidant, an isotonic agent, a buffer, a coating agent, a sweetening agent, a solubilizer, a base, a dispersion, a wetting agent, a suspending agent, a stabilizer, a colorant, and combinations thereof.

3. An injectable solution comprising the composition of claim 1.

4. The composition of claim 1, wherein the composition is in a form selected from the group consisting of tablets, capsules, granules, fine subtilae, powders, sublingual tablets, suppositories, ointments, injections, turbid liquids, suspensions, syrups, and sprays.

5. A food product comprising the composition of claim 1, wherein the food product is selected from the group consisting of candy, cracker, gum, ice cream, noodle, bread, and beverage.

6. A method of improving cognitive function or treating cognitive impairment comprising administering to a subject in need thereof an effective amount of the composition of claim 1.

7. A method of improving cognitive function or treating cognitive impairment comprising administering to a subject in need thereof an effective amount of the composition of claim 1.

8. A composition comprising:
a fermentation product as an active ingredient, wherein the fermentation product comprises *Lactobacillus pentosus* var. *plantarum* C29 strain (deposit number: KCCM11291P) and is obtained by inoculating a specific substrate with *Lactobacillus pentosus* var. *plantarum* C29 strain,
wherein the specific substrate comprises defatted soybean powder.

9. The composition of claim 8, wherein the specific substrate is sterilized prior to inoculation with *Lactobacillus pentosus* var. *plantarum* C29 strain.

10. The composition of claim 8, wherein the specific substrate is sterilized by heating to a temperature of 100° C. or more for 15 minutes to 1 hour.

11. An injectable solution comprising the composition of claim 8.

12. The composition of claim 8, wherein the composition is in a form selected from the group consisting of tablets, capsules, granules, fine subtilae, powders, sublingual tablets, suppositories, ointments, injections, turbid liquids, suspensions, syrups, and sprays.

13. A food product comprising the composition of claim 8, wherein the food product is selected from the group consisting of candy, cracker, gum, ice cream, noodle, bread, and beverage.

14. The composition of claim 8, further comprising a pharmaceutically acceptable carrier.

\* \* \* \* \*

SEQUENCE LISTING

```
<160> NUMBER OF SEQ ID NOS: 2

<210> SEQ ID NO 1
<211> LENGTH: 1428
<212> TYPE: DNA
<213> ORGANISM: Lactobacillus pentosus var. plantarum

<400> SEQUENCE: 1
acgaactctg gtattgattg gtgcttgcat catgatttac atttgagtga gtggcgaact      60
ggtgagtaac acgtgggaaa cctgcccaga agcgggggat aacacctgga aacagatgct     120
aataccgcat aacaacttgg accgcatggt ccgagtttga aagatggctt cggctatcac     180
ttttggatgg tcccgcggcg tattagctag atggtggggt aacggctcac catggcaatg     240
atacgtagcc gacctgagag ggtaatcggc cacattggga ctgagacacg gcccaaactc     300
ctacgggagg cagcagtagg gaatcttcca caatggacga aagtctgatg gagcaacgcc     360
gcgtgagtga agaagggttt cggctcgtaa aactctgttg ttaaagaaga acatatctga     420
gagtaactgt tcaggtattg acggtattta accagaaagc cacggctaac tacgtgccag     480
cagccgcggt aatacgtagg tggcaagcgt tgtcccggat ttattgggcg taaagcgagc     540
gcaggcggtt ttttaagtct gatgtgaaag ccttcggctc aaccgaagaa gtgcatcgga     600
```

```
aactgggaaa cttgagtgca gaagaggaca gtggaactcc atgtgtagcg gtgaaatgcg      660
tagatatatg gaagaacacc agtggcgaag gcggctgtct ggtctgtaac tgacgctgag      720
gctcgaaagt atgggtagca aacaggatta gataccctgg tagtccatac cgtaaacgat      780
gaatgctaag tgttggaggg tttccgccct tcagtgctgc agctaacgca ttaagcattc      840
cgcctgggga gtacggccgc aaggctgaaa ctcaaaggaa ttgacggggg cccgcacaag      900
cggtggagca tgtggtttaa ttcgaagcta cgcgaagaac cttaccaggt cttgacatac      960
tatgcaaatc taagagatta gacgttccct tcggggacat ggatacaggt ggtgcatggt     1020
tgtcgtcagc tcgtgtcgtg agatgttggg ttaagtcccg caacgagcgc aacccttatt     1080
atcagttgcc agcattaagt tgggcactct ggtgagactg ccggtgacaa accggaggaa     1140
ggtggggatg acgtcaaatc atcatgcccc ttatgacctg gctacacac gtgctacaat      1200 ggatggtaca acgagttgcg aactcgcgag agtaagctaa tctcttaaag ccattctcag     1260
ttcggattgt aggctgcaac tcgcctacat gaagtcggaa tcgctagtaa tcgcggatca     1320
gcatgccgcg gtgaatacgt tcccgggcct tgtacacacc gcccgtcaca ccatgagagt     1380
ttgtaacacc caaagtcggt ggggtaacct tttaggaacc agccgcct                  1428

<210> SEQ ID NO 2
<211> LENGTH: 893
<212> TYPE: DNA
<213> ORGANISM: Lactobacillus curvatus

<400> SEQUENCE: 2
agtcgtaaca aggtaaccgt agaagtcttg attcgataac atttgagtga gtggcggacg       60
ggtgagtaac acgtgggtaa cctgccctaa agtgggggat aacatttgga aacagatgct      120
ataccgcata aaacctagca ccgcatggtg caaggttgaa agatggtttc ggctatcact      180
ttaggatgga cccgcggtgc attagttagt tggtgaggta aaggctcacc aagaccgtga      240
tgcatagccg acctgagagg gtaatcggcc acactgggac tgagacacgg cccagactcc      300
tacgggaggc agcagtaggg aatcttccac aatggacgaa agtctgatgg agcaacgccg      360
cgtgagtgaa gaaggttttc ggatcgtaaa actctgttgt tggagaagaa cgtatttgat      420
agtaactgat caggtagtga cggtatccaa ccagaaagcc acggctaact acgtgccagc      480
agccgcggta atacgtaggt ggcaagcgtt gtccggattt attgggcgta aagcgagcgc      540
aggcggtttc ttaagtctga tgtgaaagcc ttcggctcaa ccgaagaagt gcatcggaaa      600
ctgggaaact tgagtgcaga gaggacagt ggaactccat gtgtagcggt gaaatgcgta       660
gatatatgga agaaccagt ggcgaaggc ggctgtctgg tctgtaactg acgctgaggc        720
tcgaaagcat gggtagcaaa caggattaga taccctggta gtccatgccg taaacgatga      780
gtgctaggtg ttggagggtt tccgcccttc agtgccgcag ctaacgcatt aagcactccg      840
cctggggagt acgaccgcaa ggttgaaact caaaggaatt gacggggcc cgc              893
```